US012208157B2

(12) United States Patent
Constantine et al.

(10) Patent No.: US 12,208,157 B2
(45) Date of Patent: Jan. 28, 2025

(54) SOLID COSMETIC COMPOSITION CONTAINING VEGETABLE BUTTERS

(71) Applicant: COSMETIC WARRIORS LIMITED, Poole (GB)

(72) Inventors: Mark Constantine, Poole (GB); Margaret Joan Constantine, Poole (GB); Helen Elizabeth Ambrosen, Poole (GB); Rowena Jacqueline Bird, Poole (GB)

(73) Assignee: COSMETIC WARRIORS LIMITED, Poole (GB)

( * ) Notice: Subject to any disclaimer, the term of this patent is extended or adjusted under 35 U.S.C. 154(b) by 752 days.

(21) Appl. No.: 17/416,309

(22) PCT Filed: Dec. 19, 2019

(86) PCT No.: PCT/GB2019/053631
§ 371 (c)(1),
(2) Date: Jun. 18, 2021

(87) PCT Pub. No.: WO2020/128490
PCT Pub. Date: Jun. 25, 2020

(65) Prior Publication Data
US 2022/0071890 A1    Mar. 10, 2022

(30) Foreign Application Priority Data
Dec. 20, 2018    (GB) .................................... 1820878

(51) Int. Cl.
| A61K 8/92 | (2006.01) |
| A61K 8/02 | (2006.01) |
| A61K 8/06 | (2006.01) |
| A61K 8/36 | (2006.01) |
| A61K 8/37 | (2006.01) |
| A61K 8/73 | (2006.01) |
| A61Q 1/10 | (2006.01) |
| A61Q 19/00 | (2006.01) |
| A61Q 19/10 | (2006.01) |

(52) U.S. Cl.
CPC ............ *A61K 8/922* (2013.01); *A61K 8/0216* (2013.01); *A61K 8/06* (2013.01); *A61K 8/361* (2013.01); *A61K 8/375* (2013.01); *A61K 8/73* (2013.01); *A61Q 1/10* (2013.01); *A61Q 19/007* (2013.01); *A61Q 19/10* (2013.01); *A61K 2800/95* (2013.01)

(58) Field of Classification Search
CPC ............ A61K 8/922; A61K 8/06; A61Q 1/10
See application file for complete search history.

(56) References Cited

U.S. PATENT DOCUMENTS

| 5,997,889 A | 12/1999 | Durr et al. |
| 2007/0196298 A1 | 8/2007 | Kostick et al. |
| 2009/0142289 A1 * | 6/2009 | Arditty ................... A61Q 1/10 |
| | | 424/70.7 |
| 2013/0280353 A1 * | 10/2013 | Pereira ................... A23K 50/10 |
| | | 424/725 |
| 2017/0258706 A1 | 9/2017 | Hili |
| 2017/0358706 A1 | 9/2017 | Hili et al. |
| 2017/0354589 A1 | 12/2017 | Edgett et al. |
| 2018/0153793 A1 | 6/2018 | Constantine et al. |

FOREIGN PATENT DOCUMENTS

| BE | 598741 A | 1/1961 | |
| CN | 105796374 A | 7/2016 | |
| CN | 107557190 A | 1/2018 | |
| EP | 1467697 A1 | 10/2004 | |
| GB | 2537650 A * | 10/2016 | ............... A61K 8/02 |
| JP | 2005-516026 A | 6/2005 | |
| JP | 2008-247882 A | 10/2008 | |
| JP | 2015-129183 A | 7/2015 | |
| JP | 2018-513151 A | 5/2018 | |
| JP | 2018-521997 A | 8/2018 | |
| KR | 20190024043 A | 3/2019 | |
| WO | 2003030882 A1 | 4/2003 | |
| WO | 2016020435 A | 2/2016 | |
| WO | 2016209640 A1 | 12/2016 | |
| WO | WO-2018098542 A1 * | 6/2018 | |

OTHER PUBLICATIONS

International Search Report and Written Opinion for PCT/GB2019/053631 (Mar. 12, 2020).
Search Report Under Section 17(5) for British Patent Application No. 1820878.5 (Jun. 28, 2019).
Japanese Notification of reason for refusal received for JP Serial No. 2021-534651, 5 pgs.

* cited by examiner

*Primary Examiner* — Andrew S Rosenthal
(74) *Attorney, Agent, or Firm* — Merchant & Gould P.C.

(57) ABSTRACT

A solid cosmetic composition includes one or more vegetable butters in a total amount of 20 to 80 wt. % based on the cosmetic composition. The composition also has one or more waxes in a total amount of 3 to 4 wt. % based on the cosmetic composition. The composition also includes one or more emulsifying materials in a total amount of 5 to 40 wt. % based on the cosmetic composition.

15 Claims, 1 Drawing Sheet

SOLID COSMETIC COMPOSITION CONTAINING VEGETABLE BUTTERS

This application is a National Stage of PCT/GB2019/053631, filed Dec. 19, 2019, which claims benefit of British Patent Application No. 1820878.5, filed Dec. 20, 2018, which applications are incorporated herein by reference. To the extent appropriate, a claim of priority is made to each of the above-disclosed applications.

FIELD OF THE INVENTION

The present invention relates to a solid cosmetic product, a process for producing said products, and products prepared by the process.

BACKGROUND TO THE INVENTION

The present invention relates to products particularly those for use in contact with the human body.

In its broadest definition, cosmetics are a range of products which are used to enhance or maintain the appearance or fragrance of the human body. They include make up, moisturisers fragrances such as perfume, bath products, dental products, oral hygiene products such as toothpaste, cleansing products such as soap, and hair products such as shampoo and conditioners. Many of these products have traditionally been supplied in the form of a liquid or paste and such liquids or pastes asked by necessity be stored within a container. Although traditionally these containers may have been reusable, since the introduction of mass packaging the containers have typically been single use containers, often made from plastic materials. Irrespective of whether containers are recycled, the use of unnecessary packaging is inherently damaging to the environment at least because of the energy required to manufacture and transport the packaging. Furthermore the delivery of such cosmetic products in the form of a liquid has encouraged manufacturers to include unnecessary amounts of water in products. This results in further energy usage for the transportation of the additional water.

SUMMARY OF THE INVENTION

In one aspect there is provided a solid cosmetic composition, wherein the cosmetic composition comprises
(a) one or more vegetable butters in a total amount of 20 to 80 wt. % based on the cosmetic composition;
(b) one or more waxes in a total amount of 3 to 45 wt. % based on the cosmetic composition; and
(c) one or more emulsifying materials in a total amount of 5 to 40 wt. % based on the cosmetic composition.

In one aspect there is provided a process for the production of a solid cosmetic composition, wherein the process comprises the steps of:
(a) providing a solid cosmetic composition comprising;
 (i) one or more vegetable butters in a total amount of 20 to 80 wt. % based on the cosmetic composition;
 (ii) one or more waxes in a total amount of 3 to 45 wt. % based on the cosmetic composition; and
 (iii) one or more emulsifying materials in a total amount of 5 to 40 wt. % based on the cosmetic composition;
(b) heating the solid cosmetic composition to make the cosmetic composition flowable;
(c) allowing the flowable cosmetic composition to set to form the solid cosmetic composition.

In one aspect there is provided a solid cosmetic composition prepared by 3D printing, wherein the cosmetic composition comprises
(a) one or more vegetable butters in a total amount of 20 to 80 wt. % based on the cosmetic composition;
(b) one or more waxes in a total amount of 3 to 45 wt. % based on the cosmetic composition; and
(c) one or more emulsifying materials in a total amount of 5 to 40 wt. % based on the cosmetic composition.

In one aspect there is provided a product obtained or obtainable by a process comprises the steps of:
(a) providing a solid cosmetic composition comprising;
 (i) one or more vegetable butters in a total amount of 20 to 80 wt. % based on the cosmetic composition;
 (ii) one or more waxes in a total amount of 3 to 45 wt. % based on the cosmetic composition; and
 (iii) one or more emulsifying materials in a total amount of 5 to 40 wt. % based on the cosmetic composition;
(b) heating the solid cosmetic composition to make the cosmetic composition flowable;
(c) allowing the flowable cosmetic composition to set to form the solid cosmetic composition.

In one aspect there is provided a cosmetic method comprising contacting the skin or hair of a user with a solid cosmetic composition, wherein the cosmetic composition comprises
(a) one or more vegetable butters in a total amount of 20 to 80 wt. % based on the cosmetic composition;
(b) one or more waxes in a total amount of 3 to 45 wt. % based on the cosmetic composition; and
(c) one or more emulsifying materials in a total amount of 5 to 40 wt. % based on the cosmetic composition.

For ease of reference, these and further aspects of the present invention are now discussed under appropriate section headings. However, the teachings under each section are not necessarily limited to each particular section.

Advantages

We have identified that by providing a particular balance of vegetable butters, waxes and emulsifying materials one may form solid cosmetic products which products both address the environmental concerns of non-solid products but also provide a product which is more appealing to the end user. In particular, the present invention may allow for the formation of products having desirable properties such as being handled without disintegration of the solid product. The present composition may be formed into the desired solid cosmetic products through 'traditional' means such as use of a mould or may also be suitable for 3D printing. In both aspects, the present invention may allow for the formation of products having intricate or complex shapes and/or fine or detailed finishing. When 3D printing is utilised, for example, products made in accordance with the present invention may contain not only angles such as obtuse angles which would be impossible to release from mould but may contain interlocking or cooperating parts and other such intricate designs. The present invention may also allow for the preparation of products, for example, by the operation of a 3D printing process, in which the product cools and solidifies at a rate and/or in a manner which allows for the rapid production of products and for the production of products which are aesthetically acceptable to end consumers.

In one embodiment which exemplifies the advantages of the invention, the present composition has be used to create solid a makeup product, namely mascara. The preparation of this product removes the need for packaging. It may be considered that the product per se acts as its own container. The present tailored composition is capable of being moulded or 3D printed whilst also giving a final mascara product which retains the required cosmetic properties. This offers a significant advantages over present mascaras which are most commonly sold as a packaged liquid together with an applicator brush. In such products, as a result of the elaborate packaging (exacerbated by them often holding a small amount of product), a large amount of plastic waste is created which cannot be widely recycled. In contrast, a solid mascara has been provided so to mimic the look and function of a mascara container such that it can used with, and hold, any suitable existing eyelash brush. In use, the user slightly simply wets a brush and rubs it along the internal surface of the mascara to release the pigment.

As will be appreciated, other cosmetic products may be prepared using the present cosmetic composition. These further products may also 'form their own container' and this may be configured based on the final use of the cosmetic product. For example the product need not contain pigments. The present composition may be used for the preparation of products such as eye lash conditioners, facial make-up such as foundations, body make-up, hair colouring, massage bars and many others.

DESCRIPTION OF DRAWINGS

The present teachings will now be described by way of example only with reference to the following figures.

DETAILED DESCRIPTION

Figure 1A:
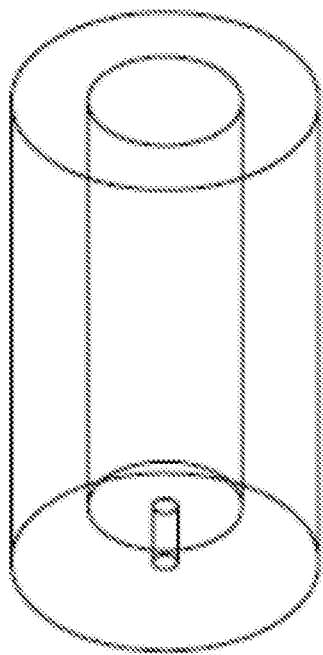
FIG. 1a is a 3D model of a solid mascara prepared in accordance with the present invention.

As discussed herein, the present invention provides each of
(1) a solid cosmetic composition, wherein the cosmetic composition comprises
   (a) one or more vegetable butters in a total amount of 20 to 80 wt. % based on the cosmetic composition;
   (b) one or more waxes in a total amount of 3 to 45 wt. % based on the cosmetic composition; and
   (c) one or more emulsifying materials in a total amount of 5 to 40 wt. % based on the cosmetic composition.
(2) a product obtained or obtainable by a process comprises the steps of:
   (a) providing a solid cosmetic composition comprising;
      (i) one or more vegetable butters in a total amount of 5 to 80 wt. % based on the cosmetic composition;
      (ii) one or more waxes in a total amount of 3 to 45 wt. % based on the cosmetic composition; and
      (iii) one or more emulsifying materials in a total amount of 5 to 40 wt. % based on the cosmetic composition;
   (b) heating the solid cosmetic composition to make the cosmetic composition flowable;
   (c) allowing the flowable cosmetic composition to set to form the solid cosmetic composition.

It will be understood by one skilled in the art that the nature of a cosmetic product means that the product is not edible. By the term edible it is meant a product which is fit to be eaten as food. Products which may be swallowed but are not suitable to be food, for example toothpaste or mouthwash, are not considered to be edible.

The solid products of the present invention are compositions which can substantially sustain their physical shape when unsupported by external means, e.g. packaging etc. Thus, they are considered to be solid, solid-like, in solid form or in solid-like form at room temperature. For the avoidance of doubt the solid product must remain substantially solid at up to 25° C.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

Due to the solid form of the compositions of the present invention, external packaging is not required to maintain the shape of the composition.

Vegetable Butters

As discussed herein the solid cosmetic composition comprises one or more vegetable butters in a total amount of 20 to 80 wt. % based on the cosmetic composition. In one aspect the solid cosmetic composition comprises one or more vegetable butters in a total amount of 20 to 75 wt. % based on the cosmetic composition. In one aspect the solid cosmetic composition comprises one or more vegetable butters in a total amount of 20 to 70 wt. % based on the cosmetic composition. In one aspect the solid cosmetic composition comprises one or more vegetable butters in a total amount of 20 to 65 wt. % based on the cosmetic composition. In one aspect the solid cosmetic composition comprises one or more vegetable butters in a total amount of 20 to 60 wt. % based on the cosmetic composition. In one aspect the solid cosmetic composition comprises one or more vegetable butters in a total amount of 20 to 55 wt. % based on the cosmetic composition. In one aspect the solid cosmetic composition comprises one or more vegetable butters in a total amount of 20 to 50 wt. % based on the cosmetic composition. In one aspect the solid cosmetic composition comprises one or more vegetable butters in a total amount of 20 to 45 wt. % based on the cosmetic composition. In one aspect the solid cosmetic composition comprises one or more vegetable butters in a total amount of 20 to 40 wt. % based on the cosmetic composition. In one aspect the solid cosmetic composition comprises one or more vegetable butters in a total amount of 20 to 35 wt. % based on the cosmetic composition.

In one aspect the solid cosmetic composition comprises one or more vegetable butters in a total amount of 25 to 80 wt. % based on the cosmetic composition. In one aspect the solid cosmetic composition comprises one or more vegetable butters in a total amount of 30 to 80 wt. % based on the cosmetic composition. In one aspect the solid cosmetic composition comprises one or more vegetable butters in a total amount of 35 to 80 wt. % based on the cosmetic composition.

In one aspect the solid cosmetic composition comprises one or more vegetable butters in a total amount of 20 to 50 wt. % based on the cosmetic composition. In one aspect the solid cosmetic composition comprises one or more vegetable butters in a total amount of 25 to 45 wt. % based on the cosmetic composition. In one aspect the solid cosmetic composition comprises one or more vegetable butters in a total amount of 30 to 40 wt. % based on the cosmetic composition.

In one aspect, the solid cosmetic composition comprises one vegetable butter. In one aspect, the solid cosmetic composition comprises a mixture of vegetable butters.

The solid cosmetic composition may comprise any suitable one or more vegetable butters. In one aspect the one or more vegetable butters are selected from Cocoa butter, Illipe butter, Murumuru butter, Kokum butter, Aloe butter, Avocado butter, Cupuacu butter, Macadamia Nut butter, Mango butter, Olive butter, Shea butter, Coconut butter, Pumpkin Seed butter, Peanut butter, Almond butter, Coffee Bean butter, Refined butter, Hemp Seed butter, Mochacchino butter, Pistachio Nut butter, Shealoe butter and mixtures thereof. In one aspect, the one or more vegetable butters are selected from Cocoa butter, Illipe butter, Cupuacu butter and mixtures thereof.

In one aspect, the solid cosmetic composition comprises at least Cocoa butter. We have found that cocoa butter is particularly advantageous due to its low melting temperature which allows rapid solidification without requiring a high melting temperature. We have also found that cocoa butter is particularly advantageous for use in 3D printing due to its low melting temperature which allows controlled deposition without requiring a high nozzle temperature. Furthermore, and importantly, it provides good solidification on cooling, for example in 3D printing on contact with the substrate once printed. In one aspect, the solid cosmetic composition comprises at least Illipe butter. We have found that Illipe butter, which is a slightly harder butter, is particularly advantageous because it will not run or smudge e.g. when used on the face or as a mascara. We have also found that it allows for 3D printing. In one aspect, the solid cosmetic composition comprises at least Cupuacu butter. We have found that Cupuacu butter is particularly advantageous because of its moisturising and conditioning properties. In one aspect, the solid cosmetic composition comprises at least Cocoa butter and Illipe butter. In one aspect, the solid cosmetic composition comprises at least Cocoa butter and Cupuacu butter. In one aspect, the solid cosmetic composition comprises at least Illipe butter and Cupuacu butter. In one aspect, the solid cosmetic composition comprises Cocoa butter, Illipe butter, and Cupuacu butter. In one aspect, the vegetable butters present in the solid cosmetic composition consist of Cocoa butter, Illipe butter and Cupuacu butter.

As discussed herein in one aspect, the solid cosmetic composition comprises at least Cocoa butter. The Cocoa butter may be present in any suitable amount. In one aspect, Cocoa butter is present in an amount of 2 to 40 wt. % based on the cosmetic composition. In one aspect, Cocoa butter is present in an amount of 2 to 35 wt. % based on the cosmetic composition. In one aspect, Cocoa butter is present in an amount of 2 to 30 wt. % based on the cosmetic composition. In one aspect, Cocoa butter is present in an amount of 2 to 25 wt. % based on the cosmetic composition. In one aspect, Cocoa butter is present in an amount of 2 to 20 wt. % based on the cosmetic composition. In one aspect, Cocoa butter is present in an amount of 2 to 15 wt. % based on the cosmetic composition. In one aspect, Cocoa butter is present in an amount of 5 to 15 wt. % based on the cosmetic composition.

As discussed herein in one aspect, the solid cosmetic composition comprises at least Illipe butter. The Illipe butter may be present in any suitable amount. In one aspect, Illipe butter is present in an amount of 2 to 40 wt. % based on the cosmetic composition. In one aspect, Illipe butter is present in an amount of 2 to 35 wt. % based on the cosmetic composition. In one aspect, Illipe butter is present in an amount of 2 to 30 wt. % based on the cosmetic composition. In one aspect, Illipe butter is present in an amount of 2 to 25 wt. % based on the cosmetic composition. In one aspect, Illipe butter is present in an amount of 2 to 20 wt. % based on the cosmetic composition. In one aspect, Illipe butter is present in an amount of 2 to 15 wt. % based on the cosmetic composition. In one aspect, Illipe butter is present in an amount of 5 to 15 wt. % based on the cosmetic composition.

As discussed herein in one aspect, the solid cosmetic composition comprises at least Cupuacu butter. The Cupuacu butter may be present in any suitable amount. In one aspect, Cupuacu butter is present in an amount of 1 to 8 wt. % based on the cosmetic composition. In one aspect, Cupuacu butter is present in an amount of 1 to 7 wt. % based on the cosmetic composition. In one aspect, Cupuacu butter is present in an amount of 1 to 6 wt. % based on the cosmetic composition. In one aspect, Cupuacu butter is present in an amount of 1 to 5 wt. % based on the cosmetic composition. In one aspect, Cupuacu butter is present in an amount of 2 to 8 wt. % based on the cosmetic composition. In one aspect, Cupuacu butter is present in an amount of 3 to 8 wt. % based on the cosmetic composition. In one aspect, Cupuacu butter is present in an amount of 4 to 8 wt. % based on the cosmetic composition. In one aspect, Cupuacu butter is present in an amount of 5 to 8 wt. % based on the cosmetic composition.

Each of the above amounts of Cocoa butter, Illipe butter and Cupuacu butter may be combined. In one aspect, the solid cosmetic composition comprises (i) Cocoa butter in an amount of 2 to 40 wt. % based on the cosmetic composition; (ii) Illipe butter in an amount of 2 to 40 wt. % based on the cosmetic composition; and (iii) Cupuacu butter in an amount of 1 to 8 wt. % based on the cosmetic composition. In one aspect, the solid cosmetic composition comprises (i) Cocoa butter in an amount of 3 to 25 wt. % based on the cosmetic composition; (ii) Illipe butter in an amount of 3 to 25 wt. % based on the cosmetic composition; and (iii) Cupuacu butter in an amount of 2 to 4.5 wt. % based on the cosmetic composition.

Waxes

As discussed herein the solid cosmetic composition comprises one or more waxes in a total amount of 3 to 45 wt. % based on the cosmetic composition. We have found that the inclusion of one or more waxes in a total amount of 3 to 45 wt. % provides a composition which is not only susceptible to flow and therefor suitable for 3D printing or moulding but on cooling hardens to provide an acceptable texture for the cosmetic product. In particular, we have found that the inclusion of the wax results in a product which will not transfer onto the fingers of the user when product is held, for example in the case of a mascara the fingers of the user will not be stained. However, using a small amount of water to moisten the composition allows for application by the user. As will be appreciated by one skilled in the art, the one or more waxes are different to the one or more emulsifying materials recited herein. The one or more waxes do not act as emulsifiers (otherwise they would be classed as emulsifying materials) and therefore they may be considered to be non-emulsifying waxes. References in the present specification to wax or to one or more waxes may be read to be non-emulsifying wax or to one or more non-emulsifying waxes. In one aspect the solid cosmetic composition comprises one or more waxes in a total amount of 3 to 40 wt. % based on the cosmetic composition. In one aspect the solid cosmetic composition comprises one or more waxes in a total amount of 3 to 35 wt. % based on the cosmetic composition. In one aspect the solid cosmetic composition comprises one or more waxes in a total amount of 3 to 30 wt. % based on the cosmetic composition. In one aspect the solid cosmetic composition comprises one or more waxes in a total amount of 3 to 25 wt. % based on the cosmetic composition. In one aspect the solid cosmetic composition comprises one or more waxes in a total amount of 3 to 20 wt. % based on the cosmetic composition. In one aspect the solid cosmetic composition comprises one or more waxes in a total amount of 3 to 15 wt. % based on the cosmetic composition. In one aspect the solid cosmetic composition comprises one or more waxes in a total amount of 3 to 12 wt. % based on the cosmetic composition. In one aspect the solid cosmetic composition comprises one or more waxes in a total amount of 3 to 10 wt. % based on the cosmetic composition. In one aspect the solid cosmetic composition comprises one or more waxes in a total amount of 3 to 8 wt. % based on the cosmetic composition. In one aspect the solid cosmetic composition comprises one or more waxes in a total amount of 3 to 6 wt. % based on the cosmetic composition.

In one aspect the solid cosmetic composition comprises one or more waxes in a total amount of 5 to 40 wt. % based on the cosmetic composition. In one aspect the solid cosmetic composition comprises one or more waxes in a total amount of 5 to 35 wt. % based on the cosmetic composition. In one aspect the solid cosmetic composition comprises one or more waxes in a total amount of 5 to 30 wt. % based on the cosmetic composition. In one aspect the solid cosmetic composition comprises one or more waxes in a total amount of 5 to 25 wt. % based on the cosmetic composition. In one aspect the solid cosmetic composition comprises one or more waxes in a total amount of 5 to 20 wt. % based on the cosmetic composition. In one aspect the solid cosmetic composition comprises one or more waxes in a total amount of 5 to 15 wt. % based on the cosmetic composition.

In one aspect the solid cosmetic composition comprises one or more waxes in a total amount of 8 to 45 wt. % based on the cosmetic composition. In one aspect the solid cosmetic composition comprises one or more waxes in a total amount of 10 to 45 wt. % based on the cosmetic composition. In one aspect the solid cosmetic composition comprises one or more waxes in a total amount of 12 to 45 wt. % based on the cosmetic composition. In one aspect the solid cosmetic composition comprises one or more waxes in a total amount of 15 to 45 wt. % based on the cosmetic composition.

In one aspect the solid cosmetic composition comprises one or more waxes in a total amount of 10 to 40 wt. % based on the cosmetic composition. In one aspect the solid cosmetic composition comprises one or more waxes in a total amount of 10 to 35 wt. % based on the cosmetic composition. In one aspect the solid cosmetic composition comprises one or more waxes in a total amount of 10 to 30 wt. % based on the cosmetic composition. In one aspect the solid cosmetic composition comprises one or more waxes in a total amount of 10 to 25 wt. % based on the cosmetic composition. In one aspect the solid cosmetic composition comprises one or more waxes in a total amount of 10 to 20 wt. % based on the cosmetic composition.

In one aspect, the solid cosmetic composition comprises one wax. In one aspect, the solid cosmetic composition comprises a mixture of waxes.

The solid cosmetic composition may comprise any suitable one or more waxes. In one aspect the one or more waxes are selected from carnauba wax, candelilla, Japan wax, beeswax, rapeseed wax, sunflower wax, orange peel wax, rose wax, paraffin wax, ozocerite wax and mixtures thereof. In one aspect the one or more waxes are selected from carnauba wax, Japan wax and mixtures thereof. We have found that carnauba wax provides a glossy sheen to the cosmetic product when applied by the user whilst Japan wax has a mattifying effect.

In one aspect, the solid cosmetic composition comprises at least carnauba wax. In one aspect, the solid cosmetic composition comprises at least Japan wax. In one aspect, the solid cosmetic composition comprises at least carnauba wax and Japan wax. In one aspect, the waxes present in the solid cosmetic composition consist of carnauba wax and Japan wax. In one aspect, the waxes present in the solid cosmetic composition consist of carnauba wax. In one aspect, the waxes present in the solid cosmetic composition consist of Japan wax.

As discussed herein in one aspect, the solid cosmetic composition comprises at least carnauba wax. The carnauba wax may be present in any suitable amount. In one aspect, carnauba wax is present in an amount of 3 to 30 wt. % based on the cosmetic composition. In one aspect, carnauba wax is present in an amount of 4 to 30 wt. % based on the cosmetic composition. In one aspect, carnauba wax is present in an amount of 3 to 25 wt. % based on the cosmetic composition. In one aspect, carnauba wax is present in an amount of 4 to 25 wt. % based on the cosmetic composition. In one aspect, carnauba wax is present in an amount of 3 to 20 wt. % based on the cosmetic composition. In one aspect, carnauba wax is present in an amount of 4 to 20 wt. % based on the cosmetic composition. In one aspect, carnauba wax is present in an amount of 3 to 15 wt. % based on the cosmetic composition. In one aspect, carnauba wax is present in an amount of 4 to 15 wt. % based on the cosmetic composition. In one aspect, carnauba wax is present in an amount of 5 to 30 wt. % based on the cosmetic composition. In one aspect, carnauba wax is present in an amount of 10 to 30 wt. % based on the cosmetic composition. In one aspect, carnauba wax is present in an amount of 12 to 30 wt. % based on the cosmetic composition. In one aspect, carnauba wax is present in an amount of 5 to 25 wt. % based on the cosmetic composition. In one aspect, carnauba wax is present in an amount of 5 to 20 wt. % based on the cosmetic composition. In one aspect, carnauba wax is present in an amount of 5 to 15 wt. % based on the cosmetic composition. In one aspect, carnauba wax is present in an amount of 10 to 15 wt. % based on the cosmetic composition.

As discussed herein in one aspect, the solid cosmetic composition comprises at least Japan wax. The Japan wax may be present in any suitable amount. In one aspect, Japan wax is present in an amount of 1 to 16 wt. % based on the cosmetic composition. In one aspect, Japan wax is present in an amount of 1 to 14 wt. % based on the cosmetic composition. In one aspect, Japan wax is present in an amount of 1 to 12 wt. % based on the cosmetic composition. In one aspect, Japan wax is present in an amount of 1 to 10 wt. % based on the cosmetic composition. In one aspect, Japan wax is present in an amount of 1 to 8 wt. % based on the cosmetic composition. In one aspect, Japan wax is present in an amount of 1 to 6 wt. % based on the cosmetic composition. In one aspect, Japan wax is present in an amount of 1 to 4 wt. % based on the cosmetic composition. In one aspect, Japan wax is present in an amount of 2 to 16 wt. % based on the cosmetic composition. In one aspect, Japan wax is present in an amount of 2 to 14 wt. % based on the cosmetic composition. In one aspect, Japan wax is present in an amount of 2 to 12 wt. % based on the cosmetic composition. In one aspect, Japan wax is present in an amount of 2 to 10 wt. % based on the cosmetic composition. In one aspect, Japan wax is present in an amount of 2 to 8 wt. % based on the cosmetic composition. In one aspect, Japan wax is present in an amount of 2 to 6 wt. % based on the cosmetic composition. In one aspect, Japan wax is present in an amount of 2 to 4 wt. % based on the cosmetic composition.

Each of the above amounts of carnauba wax and Japan wax may be combined. In one aspect, the solid cosmetic composition comprises (i) carnauba wax in an amount of 5 to 30 wt. % based on the cosmetic composition; and (ii) Japan wax in an amount of 1 to 16 wt. % based on the cosmetic composition. In one aspect, the solid cosmetic composition comprises (i) carnauba wax in an amount of 10 to 25 wt. % based on the cosmetic composition; and (ii) Japan wax in an amount of 2 to 8 wt. % based on the cosmetic composition.

Each of the above amounts of carnauba wax and Japan wax may be combined. In one aspect, the solid cosmetic composition comprises (i) carnauba wax in an amount of 0 to 30 wt. % based on the cosmetic composition; and (ii) Japan wax in an amount of 1 to 16 wt. % based on the cosmetic composition. In one aspect, the solid cosmetic composition comprises (i) carnauba wax in an amount of 0 to 25 wt. % based on the cosmetic composition; and (ii) Japan wax in an amount of 2 to 8 wt. % based on the cosmetic composition.

Emulsifying Materials

As discussed herein the solid cosmetic composition comprises one or more emulsifying materials in a total amount of 5 to 40 wt. % based on the cosmetic composition. As will be appreciated by one skilled in the art, the one or more emulsifying materials are different to the one or more waxes recited herein. In one aspect the solid cosmetic composition comprises one or more emulsifying materials in a total amount of 5 to 35 wt. % based on the cosmetic composition. In one aspect the solid cosmetic composition comprises one or more emulsifying materials in a total amount of 5 to 30 wt. % based on the cosmetic composition. In one aspect the solid cosmetic composition comprises one or more emulsifying materials in a total amount of 5 to 25 wt. % based on the cosmetic composition. In one aspect the solid cosmetic composition comprises one or more emulsifying materials in a total amount of 5 to 20 wt. % based on the cosmetic composition. In one aspect the solid cosmetic composition comprises one or more emulsifying materials in a total amount of 5 to 15 wt. % based on the cosmetic composition.

In one aspect the solid cosmetic composition comprises one or more emulsifying materials in a total amount of 8 to 40 wt. % based on the cosmetic composition. In one aspect the solid cosmetic composition comprises one or more emulsifying materials in a total amount of 10 to 40 wt. % based on the cosmetic composition. In one aspect the solid cosmetic composition comprises one or more emulsifying materials in a total amount of 12 to 40 wt. % based on the cosmetic composition. In one aspect the solid cosmetic composition comprises one or more emulsifying materials in a total amount of 15 to 40 wt. % based on the cosmetic composition.

In one aspect the solid cosmetic composition comprises one or more emulsifying materials in a total amount of 10 to 35 wt. % based on the cosmetic composition. In one aspect the solid cosmetic composition comprises one or more emulsifying materials in a total amount of 10 to 30 wt. % based on the cosmetic composition. In one aspect the solid cosmetic composition comprises one or more emulsifying materials in a total amount of 10 to 25 wt. % based on the cosmetic composition. In one aspect the solid cosmetic composition comprises one or more emulsifying materials in a total amount of 10 to 20 wt. % based on the cosmetic composition.

In one aspect, the solid cosmetic composition comprises one emulsifying wax. In one aspect, the solid cosmetic composition comprises a mixture of emulsifying materials.

The solid cosmetic composition may comprise any suitable one or more emulsifying materials. In one aspect the one or more emulsifying materials are selected from stearic acid and salts thereof, glycerol monostearate, esters of polyethylene glycol and stearic acid, cetearyl olivate, sorbitan olivate, triethanolamine and mixtures thereof. In one aspect the one or more emulsifying materials are selected from glycerol monostearate, esters of polyethylene glycol and stearic acid, stearic acid and salts thereof, and mixtures thereof. In one aspect the one or more emulsifying materials are selected from glycerol monostearate, esters of polyethylene glycol and stearic acid, and mixtures thereof. In one aspect the one or more emulsifying materials are selected from stearic acid and salts thereof, glycerol monostearate and mixtures thereof. Esters of polyethylene glycol and stearic acid may be referred to in the art as PEG-stearate (such as PEG-100 stearate) and references in the present specification to PEG-stearate (such as PEG-100 stearate) refer to esters of polyethylene glycol and stearic acid.

The one or more emulsifying materials may comprise or may consist of one or more emulsifying waxes. As the skilled person will appreciate, an emulsifying wax is a combination of a wax material and a detergent (or surfactant). As used herein, the term "emulsifying wax" is a mixture comprising (i) a fatty acid, fatty alcohol, fatty acid ester, and mixtures thereof, and (ii) a surfactant. As used herein, the term "Emulsifying wax NF" means an emulsifying wax that conforms to the specifications of the National Formulary, and which comprises a combination of cetearyl alcohol and a polysorbate (a polyoxyethylene derivative of a fatty acid ester of sorbitan).

In some embodiments, the wax is an emulsifying wax selected from the group consisting of cetearyl alcohol and a sodium alkyl sulfate, cetearyl alcohol and a polysorbate, cetearyl alcohol and a polymer of ethylene oxide, cetearyl alcohol and ceteareth-20, cetearyl alcohol and ceteareth-30, glyceryl stearate and a polymer of ethylene oxide, cetearyl olivate and sorbitan olivate, ethoxylated cetearyl alcohols, ethoxylated stearyl alcohols, and mixtures thereof.

In some embodiments, the wax is an emulsifying wax is selected from cetearyl alcohol and sodium lauryl sulfate, cetearyl alcohol and sodium laureth sulfate, cetearyl alcohol and sodium cocsulfate, and mixtures thereof. In some embodiments, the wax is cetearyl alcohol and sodium lauryl sulfate.

In some embodiments, the wax is emulsifying wax NF. In some embodiments, the wax is cetaryl alcohol and polysorbate 60 (Polawax).

In some embodiments, the wax is an emulsifying wax selected from the group consisting of cetearyl alcohol (and) sodium lauryl sulfate, cetearyl alcohol (and) polysorbate 60, cetearyl alcohol (and) ceteareth-20, and mixtures thereof.

In one aspect, the solid cosmetic composition comprises at least stearic acid or salts thereof. In one aspect, the solid cosmetic composition comprises at least glycerol monostearate. In one aspect, the solid cosmetic composition comprises at least esters of polyethylene glycol and stearic acid. In one aspect, the solid cosmetic composition comprises at least stearic acid or salts thereof, glycerol monostearate and esters of polyethylene glycol and stearic acid. In one aspect, the solid cosmetic composition comprises at least stearic acid or salts thereof and glycerol monostearate. In one aspect, the solid cosmetic composition comprises at least stearic acid or salts thereof, and esters of polyethylene glycol and stearic acid. In one aspect, the solid cosmetic composition comprises at least glycerol monostearate and esters of polyethylene glycol and stearic acid. In one aspect, the emulsifying materials present in the solid cosmetic composition consist of esters of polyethylene glycol and stearic acid. In one aspect, the emulsifying materials present in the solid cosmetic composition consist of stearic acid or salts thereof, glycerol monostearate and esters of polyethylene glycol and stearic acid. In one aspect, the emulsifying materials present in the solid cosmetic composition consist of stearic acid or salts thereof and glycerol monostearate. In one aspect, the emulsifying materials present in the solid cosmetic composition consist of stearic acid or salts thereof, and esters of polyethylene glycol and stearic acid. In one aspect, the emulsifying materials present in the solid cosmetic composition consist of glycerol monostearate and esters of polyethylene glycol and stearic acid. In one aspect, the emulsifying materials present in the solid cosmetic composition consist of stearic acid or salts thereof. In one aspect, the emulsifying materials present in the solid cosmetic composition consist of glycerol monostearate. In one aspect, the emulsifying materials present in the solid cosmetic composition consist of esters of polyethylene glycol and stearic acid.

As discussed herein in one aspect, the solid cosmetic composition comprises at least stearic acid or salts thereof. In one aspect, the solid cosmetic composition comprises at least stearic acid. In one aspect, references to stearic acid or salts thereof in the present specification may be read to refer to stearic acid only. Suitable salts of stearic acid include the sodium and potassium salts, namely sodium stearate and potassium stearate. The stearic acid or salts thereof may be present in any suitable amount. In one aspect, the stearic acid or salts thereof is present in an amount of 2 to 18 wt. % based on the cosmetic composition. In one aspect, the stearic acid or salts thereof is present in an amount of 2 to 16 wt. % based on the cosmetic composition. In one aspect, the stearic acid or salts thereof is present in an amount of 2 to 14 wt. % based on the cosmetic composition. In one aspect, the stearic acid or salts thereof is present in an amount of 2 to 12 wt. % based on the cosmetic composition. In one aspect, the stearic acid or salts thereof is present in an amount of 2 to 10 wt. % based on the cosmetic composition. In one aspect, the stearic acid or salts thereof is present in an amount of 2 to 8 wt. % based on the cosmetic composition. In one aspect, the stearic acid or salts thereof is present in an amount of 2 to 6 wt. % based on the cosmetic composition. In one aspect, the stearic acid or salts thereof is present in an amount of 2 to 5 wt. % based on the cosmetic composition. In one aspect, the stearic acid or salts thereof is present in an amount of 3 to 18 wt. % based on the cosmetic composition. In one aspect, the stearic acid or salts thereof is present in an amount of 4 to 18 wt. % based on the cosmetic composition. In one aspect, the stearic acid or salts thereof is present in an amount of 5 to 18 wt. % based on the cosmetic composition. In one aspect, the stearic acid or salts thereof is present in an amount of 2 to 15 wt. % based on the cosmetic composition. In one aspect, the stearic acid or salts thereof is present in an amount of 3 to 10 wt. % based on the cosmetic composition. In one aspect, the stearic acid or salts thereof is present in an amount of 4 to 7 wt. % based on the cosmetic composition.

As discussed herein in one aspect, the solid cosmetic composition comprises at least glycerol monostearate, ester of polyethylene glycol and stearic acid, or a mixture thereof. The glycerol monostearate, ester of polyethylene glycol and stearic acid, or a mixture thereof may be present in any suitable amount. In one aspect, glycerol monostearate, ester of polyethylene glycol and stearic acid, or a mixture thereof is present in an amount of 5 to 25 wt. % based on the cosmetic composition. In one aspect, glycerol monostearate, ester of polyethylene glycol and stearic acid, or a mixture thereof is present in an amount of 5 to 22 wt. % based on the cosmetic composition. In one aspect, glycerol monostearate, ester of polyethylene glycol and stearic acid, or a mixture thereof is present in an amount of 5 to 20 wt. % based on the cosmetic composition. In one aspect, glycerol monostearate, ester of polyethylene glycol and stearic acid, or a mixture thereof is present in an amount of 5 to 18 wt. % based on the cosmetic composition. In one aspect, glycerol monostearate, ester of polyethylene glycol and stearic acid, or a mixture thereof is present in an amount of 5 to 16 wt. % based on the cosmetic composition. In one aspect, glycerol monostearate, ester of polyethylene glycol and stearic acid, or a mixture thereof is present in an amount of 5 to 14 wt. % based on the cosmetic composition. In one aspect, glycerol monostearate, ester of polyethylene glycol and stearic acid, or a mixture thereof is present in an amount of 5 to 12 wt. % based on the cosmetic composition. In one aspect, glycerol monostearate, ester of polyethylene glycol and stearic acid, or a mixture thereof is present in an amount of 7 to 25 wt. % based on the cosmetic composition. In one aspect, glycerol monostearate, ester of polyethylene glycol and stearic acid, or a mixture thereof is present in an amount of 9 to 25 wt. % based on the cosmetic composition. In one aspect, glycerol monostearate, ester of polyethylene glycol and stearic acid, or a mixture thereof is present in an amount of 11 to 25 wt. % based on the cosmetic composition. In one aspect, glycerol monostearate, ester of polyethylene glycol and stearic acid, or a mixture thereof is present in an amount of 12 to 25 wt. % based on the cosmetic composition. In one aspect, glycerol monostearate, ester of polyethylene glycol and stearic acid, or a mixture thereof is present in an amount of 10 to 20 wt. % based on the cosmetic composition. In one aspect, glycerol monostearate, ester of polyethylene glycol and stearic acid, or a mixture thereof is present in an amount of 10 to 18 wt. % based on the cosmetic composition. In one aspect, glycerol monostearate, ester of polyethylene glycol and stearic acid, or a mixture thereof is present in an amount of 10 to 16 wt. % based on the cosmetic composition. In one aspect, glycerol monostearate, ester of polyethylene glycol and stearic acid, or a mixture thereof is present in an amount of 10 to 14 wt. % based on the cosmetic composition.

As discussed herein in one aspect, the solid cosmetic composition comprises at least glycerol monostearate. The glycerol monostearate may be present in any suitable amount. In one aspect, glycerol monostearate is present in an amount of 5 to 25 wt. % based on the cosmetic composition. In one aspect, glycerol monostearate is present in an amount of 5 to 22 wt. % based on the cosmetic composition. In one aspect, glycerol monostearate is present in an amount of 5 to 20 wt. % based on the cosmetic composition. In one aspect, glycerol monostearate is present in an amount of 5 to 18 wt. % based on the cosmetic composition. In one aspect, glycerol monostearate is present in an amount of 5 to 16 wt. % based on the cosmetic composition. In one aspect, glycerol monostearate is present in an amount of 5 to 14 wt. % based on the cosmetic composition. In one aspect, glycerol monostearate is present in an amount of 5 to 12 wt. % based on the cosmetic composition. In one aspect, glycerol monostearate is present in an amount of 7 to 25 wt. % based on the cosmetic composition. In one aspect, glycerol monostearate is present in an amount of 9 to 25 wt. % based on the cosmetic composition. In one aspect, glycerol monostearate is present in an amount of 11 to 25 wt. % based on the cosmetic composition. In one aspect, glycerol monostearate is present in an amount of 12 to 25 wt. % based on the cosmetic composition. In one aspect, glycerol monostearate is present in an amount of 10 to 20 wt. % based on the cosmetic composition. In one aspect, glycerol monostearate is present in an amount of 10 to 18 wt. % based on the cosmetic composition. In one aspect, glycerol monostearate is present in an amount of 10 to 16 wt. % based on the cosmetic composition. In one aspect, glycerol monostearate is present in an amount of 10 to 14 wt. % based on the cosmetic composition.

As discussed herein in one aspect, the solid cosmetic composition comprises at least one or more esters of polyethylene glycol and stearic acid. The one or more esters of polyethylene glycol and stearic acid may be present in any suitable amount. In one aspect, one or more esters of polyethylene glycol and stearic acid is present in an amount of 5 to 25 wt. % based on the cosmetic composition. In one aspect, one or more esters of polyethylene glycol and stearic acid is present in an amount of 5 to 22 wt. % based on the cosmetic composition. In one aspect, one or more esters of polyethylene glycol and stearic acid is present in an amount of 5 to 20 wt. % based on the cosmetic composition. In one aspect, one or more esters of polyethylene glycol and stearic acid is present in an amount of 5 to 18 wt. % based on the cosmetic composition. In one aspect, one or more esters of polyethylene glycol and stearic acid is present in an amount of 5 to 16 wt. % based on the cosmetic composition. In one aspect, one or more esters of polyethylene glycol and stearic acid is present in an amount of 5 to 14 wt. % based on the cosmetic composition. In one aspect, one or more esters of polyethylene glycol and stearic acid is present in an amount of 5 to 12 wt. % based on the cosmetic composition. In one aspect, one or more esters of polyethylene glycol and stearic acid is present in an amount of 7 to 25 wt. % based on the cosmetic composition. In one aspect, one or more esters of polyethylene glycol and stearic acid is present in an amount of 9 to 25 wt. % based on the cosmetic composition. In one aspect, one or more esters of polyethylene glycol and stearic acid is present in an amount of 11 to 25 wt. % based on the cosmetic composition. In one aspect, one or more esters of polyethylene glycol and stearic acid is present in an amount of 12 to 25 wt. % based on the cosmetic composition. In one aspect, one or more esters of polyethylene glycol and stearic acid is present in an amount of 10 to 20 wt. % based on the cosmetic composition. In one aspect, one or more esters of polyethylene glycol and stearic acid is present in an amount of 10 to 18 wt. % based on the cosmetic composition. In one aspect, one or more esters of polyethylene glycol and stearic acid is present in an amount of 10 to 16 wt. % based on the cosmetic composition. In one aspect, one or more esters of polyethylene glycol and stearic acid is present in an amount of 10 to 14 wt. % based on the cosmetic composition.

The polyethylene glycol of the esters of polyethylene glycol and stearic acid may have any suitable number of ethylene glycol units. In one aspect, the polyethylene glycol has from 20 to 300 ethylene glycol units. In one aspect, the polyethylene glycol has from 40 to 250 ethylene glycol units. In one aspect, the polyethylene glycol has from 40 to 200 ethylene glycol units. In one aspect, the polyethylene glycol has from 60 to 200 ethylene glycol units. In one aspect, the polyethylene glycol has from 60 to 180 ethylene glycol units. In one aspect, the polyethylene glycol has from 60 to 160 ethylene glycol units. In one aspect, the polyethylene glycol has from 60 to 140 ethylene glycol units. In one aspect, the polyethylene glycol has from 80 to 120 ethylene glycol units.

Each of the above amounts of stearic acid or salts thereof, glycerol monostearate, and esters of polyethylene glycol and stearic acid may be combined. In one aspect, the solid cosmetic composition comprises (i) stearic acid or salts thereof in a combined amount of 2 to 18 wt. % based on the cosmetic composition; and (ii) glycerol monostearate, and esters of polyethylene glycol and stearic acid in combined amount of 5 to 25 wt. % based on the cosmetic composition. In one aspect, the solid cosmetic composition comprises (i) stearic acid or salts thereof in a combined amount of 3 to 10 wt. % based on the cosmetic composition; and (ii) glycerol monostearate and esters of polyethylene glycol and stearic acid in a combined amount of 10 to 18 wt. % based on the cosmetic composition.

Each of the above amounts of stearic acid or salts thereof and glycerol monostearate may be combined. In one aspect, the solid cosmetic composition comprises (i) stearic acid or salts thereof in a combined amount of 2 to 18 wt. % based on the cosmetic composition; and (ii) glycerol monostearate in an amount of 5 to 25 wt. % based on the cosmetic composition. In one aspect, the solid cosmetic composition comprises (i) stearic acid or salts thereof in a combined amount of 3 to 10 wt. % based on the cosmetic composition; and (ii) glycerol monostearate in an amount of 10 to 18 wt. % based on the cosmetic composition.

Cosmetic Composition

The present invention provides for a solid cosmetic composition which is not limited to any particular cosmetic. In one aspect, the solid cosmetic composition is selected for make-up (such as mascara, lipstick, face primer, eyeshadow, 'baked' eyeshadow and foundation), moisturisers (such as body conditioners and face moisturisers), fragrances, bath products (such as bath melts), massage bars, cleansing products (such as facial cleansers and body scrubs), hair products (such as conditioners) and combinations thereof.

As discussed herein, in one aspect the solid cosmetic composition has an open end from which an internal surface of the solid cosmetic composition can be contacted to deliver cosmetic composition to a user. A typical shape for such a product may be a cylinder or other prism. Other shapes include flat shapes such as discs. Such a solid cosmetic composition may be used to form a mascara product. Such a mascara product may mimic the look and function of a 'traditional' mascara container such that it can be used with, and hold, any suitable existing eyelash brush. In use, the user slightly simply wets a brush and rubs it along the internal surface of the mascara to release the pigment.

In one aspect the present invention provides a solid fragrance composition.

In one aspect the present invention provides a solid skin foundation. As will be understood by one skilled in the art foundation is a skin coloured makeup applied to the face or body to create an even, uniform colour to the complexion, to cover flaws and, sometimes, to change the natural skin tone. Some foundations also function as a moisturizer, sunscreen, astringent or base layer for more complex cosmetics.

Additional Components

The solid product of the present invention may also comprise one or more cosmetically acceptable additives. The person skilled in the art is aware of a range of cosmetically acceptable additives which are suitable for incorporation into such compositions. For example, colours, pigments, binders, fillers, emulsifiers, opacifiers, perfumes, fragrances, decorative items, humectants, honey, sugars, sugar alcohols, soaps, surfactants, fruits, vegetables, clays, herbs, cereals, beans, proteins, scrubs, exfoliants, starches, preservatives, quaternary ammonium compounds, carbon dioxide effervescent components, and mixtures thereof.

In one aspect the cosmetic composition further comprises one or more vegetables oils. The one or more vegetables oils may be present in any suitable amount. In one aspect, the one or more vegetable oils are present in a total amount of 2 to 18 wt. % based on the cosmetic composition. In one aspect, the one or more vegetable oils are present in a total amount of 2 to 16 wt. % based on the cosmetic composition. In one aspect, the one or more vegetable oils are present in a total amount of 2 to 15 wt. % based on the cosmetic composition. In one aspect, the one or more vegetable oils are present in a total amount of 2 to 14 wt. % based on the cosmetic composition. In one aspect, the one or more vegetable oils are present in a total amount of 2 to 12 wt. % based on the cosmetic composition. In one aspect, the one or more vegetable oils are present in a total amount of 2 to 10 wt. % based on the cosmetic composition. In one aspect, the one or more vegetable oils are present in a total amount of 2 to 9 wt. % based on the cosmetic composition. In one aspect, the one or more vegetable oils are present in a total amount of 4 to 18 wt. % based on the cosmetic composition. In one aspect, the one or more vegetable oils are present in a total amount of 6 to 18 wt. % based on the cosmetic composition. In one aspect, the one or more vegetable oils are present in a total amount of 7 to 18 wt. % based on the cosmetic composition. In one aspect, the one or more vegetable oils are present in a total amount of 8 to 18 wt. % based on the cosmetic composition. In one aspect, the one or more vegetable oils are present in a total amount of 9 to 18 wt. % based on the cosmetic composition. In one aspect, the one or more vegetable oils are present in a total amount of 4 to 16 wt. % based on the cosmetic composition. In one aspect, the one or more vegetable oils are present in a total amount of 4 to 14 wt. % based on the cosmetic composition. In one aspect, the one or more vegetable oils are present in a total amount of 4 to 12 wt. % based on the cosmetic composition. In one aspect, the one or more vegetable oils are present in a total amount of 4 to 10 wt. % based on the cosmetic composition. In one aspect, the one or more vegetable oils are present in a total amount of 6 to 10 wt. % based on the cosmetic composition. In one aspect, the one or more vegetable oils are present in a total amount of 8 to 10 wt. % based on the cosmetic composition.

In one aspect, the solid cosmetic composition comprises one vegetable oil. In one aspect, the solid cosmetic composition comprises a mixture of vegetable oils.

The solid cosmetic composition may comprise any suitable one or more vegetable oils. In one aspect the one or more vegetable oils are selected from almond oil, jojoba oil, castor oil, olive oil, grape seed oil, argan oil, moringa oil, baobab oil, rose hip oil, kalahari melon oil, brazil nut oil, sacha inchi nut oil, corn oil, soya bean oil, sunflower oil, avocado oil, macadamia oil, pumpkin seed oil, evening primrose oil, apricot kernel oil, flaxseed oil, poppy seed oil, broccoli seed oil, rice bran oil, wheatgerm oil, and mixtures.

In one aspect, the solid cosmetic composition comprises at least castor oil. In one aspect, the vegetable oil present in the solid cosmetic composition consists of castor oil.

The colour, pigment or a mixture thereof may be selected from any suitable colours and pigments. In one aspect the cosmetic composition further comprises one or more pigments. The one or more pigments may be present in any suitable amount. In one aspect, the one or more pigments are present in a total amount of 9 to 20 wt. % based on the cosmetic composition. In one aspect, the one or more pigments are present in a total amount of 10 to 18 wt. % based on the cosmetic composition. In one aspect, the one or more pigments are present in a total amount of 10.5 to 17.5 wt. % based on the cosmetic composition. In one aspect, the one or more pigments are present in a total amount of 10 to 16 wt. % based on the cosmetic composition. In one aspect, the one or more pigments are present in a total amount of 10 to 14 wt. % based on the cosmetic composition. In one aspect, the one or more pigments are present in a total amount of 10 to 13 wt. % based on the cosmetic composition. In one aspect, the one or more pigments are present in a total amount of 10 to 12 wt. % based on the cosmetic composition. In one aspect, the one or more pigments are present in a total amount of 11 to 12 wt. % based on the cosmetic composition.

The solid cosmetic composition may comprise any suitable one or more colours or pigments. In one aspect the one or more colours or pigments are selected from titanium dioxide, yellow iron oxide, red iron oxide, talc, silica, black iron oxide, zinc oxide, synthetic fluorphlogopite, mica, borosilicate, lake pigments (such as D&C Red No. 30Al 40% pigment, or (F)D&C Yellow No. 5Al 24% pigment), ferric ferrocyanide, ultramarine, manganese violet, chromium hydroxide green, chromium oxide green, carbon black (D&C Black No 2), vegetable pigments (such as chlorophyllin, beetroot, anthocyanin, and gardenia), carmine and mixtures thereof. In one aspect, the solid cosmetic composition comprises black iron oxide. In one aspect, the pigment present in the solid cosmetic composition consists of black iron oxide.

In one aspect the cosmetic composition further comprises one or more fillers. The one or more fillers may be present in any suitable amount. In one aspect, the one or more fillers are present in a total amount of 2 to 10 wt. % based on the cosmetic composition. In one aspect, the one or more fillers are present in a total amount of 3 to 8 wt. % based on the cosmetic composition. In one aspect, the one or more fillers are present in a total amount of 4 to 8 wt. % based on the cosmetic composition. In one aspect, the one or more fillers are present in a total amount of 4.5 to 7.5 wt. % based on the cosmetic composition. In one aspect, the one or more fillers are present in a total amount of 4 to 7 wt. % based on the cosmetic composition. In one aspect, the one or more fillers are present in a total amount of 4 to 6 wt. % based on the cosmetic composition. In one aspect, the one or more fillers are present in a total amount of 4 to 5 wt. % based on the cosmetic composition.

The solid cosmetic composition may comprise any suitable one or more fillers. In one aspect the one or more fillers are selected from talc, kaolin, calamine, magnesium carbonate and mixtures thereof. In one aspect, the solid cosmetic composition comprises talc. In one aspect, the filler present in the solid cosmetic composition consists of talc.

The solid cosmetic composition may comprise any suitable one or more polymers.

In one aspect the cosmetic composition further comprises one or more polymers. The one or more polymers may be present in any suitable amount. In one aspect, the one or more polymers are present in a total amount of 0.5 to 12 wt. % based on the cosmetic composition. In one aspect, the one or more polymers are present in a total amount of 1 to 12 wt. % based on the cosmetic composition. In one aspect, the one or more polymers are present in a total amount of 2 to 12 wt. % based on the cosmetic composition. In one aspect, the one or more polymers are present in a total amount of 4 to 12 wt. % based on the cosmetic composition. In one aspect, the one or more polymers are present in a total amount of 6 to 10 wt. % based on the cosmetic composition. In one aspect, the one or more polymers are present in a total amount of 7 to 9 wt. % based on the cosmetic composition.

The solid cosmetic composition may comprise any suitable one or more polymers. In one aspect the one or more polymers are selected from polyvinylpyrrolidone (PVP), polyvinylpyrrolidone and vinyl acetate copolymer (PVP/VA), polyvinylpyrrolidone and eicosene copolymer and mixtures thereof. In one aspect the one or more polymers are selected from polyvinylpyrrolidone (PVP), polyvinylpyrrolidone and vinyl acetate copolymer (PVP/VA), and mixtures thereof. In one aspect the one or more polymers are selected from polyvinylpyrrolidone (PVP). In one aspect the one or more polymers are selected from polyvinylpyrrolidone and vinyl acetate copolymer (PVP/VA). In one aspect the one or more polymers consist of polyvinylpyrrolidone (PVP), polyvinylpyrrolidone and vinyl acetate copolymer (PVP/VA), and mixtures thereof.

In some embodiments, the solid cosmetic composition may comprise any suitable one or more polymers that exhibit excellent film-forming properties. Therefore, in some embodiments, the polymer is included in the solid cosmetic composition of the present invention as a film-forming agent.

As the skilled person will appreciate, a film-forming agent means a polymer or resin that leaves a film on the substrate to which it is applied, for example, after a solvent/vehicle carrying the film-forming agent has evaporated or absorbed into the substrate.

In some embodiments, the present composition further comprises a film-forming agent selected from the group consisting of a styrene polymer, acrylate polymer, methacrylate polymer, styrene/acrylate copolymer, styrene/acrylates/methacrylate copolymer, styrene/acrylate/ammonium methacrylate copolymer, and mixtures thereof. In some embodiments, the film-forming agent is selected from the group consisting of a styrene polymer, styrene/acrylate copolymer, styrene/acrylates/methacrylate copolymer, styrene/acrylate/ammonium methacrylate copolymer, and mixtures thereof.

In some embodiments, the film-forming agent is a styrene/acrylates/ammonium methacrylate copolymer.

In some preferred embodiments, the first polymeric species is SYNTRAN® 5760. SYNTRAN® 5760 is a mixture of styrene/acrylates/ammonium methacrylate copolymer, butylene glycol and sodium laureth-12 sulfate.

In some embodiments, the present composition further comprises a film-forming agent selected from natural polymers. In some embodiments, the present composition further comprises a film-forming agent selected from gum acacia.

In some preferred embodiments, the film-forming agent is a water-based dispersion of a copolymer formed of styrene, acrylate and ammonium methacrylate monomers that is able to function as a film-forming agent.

In some embodiments, the film-forming agent is present in the composition in an amount of from about 1 to about 50 wt. % based on the total weight of the composition. In some embodiments, the film-forming agent is present in the composition in an amount of from about 10 to about 50 wt. % based on the total weight of the composition. In some embodiments, the film-forming agent is present in the composition in an amount of from about 10 to about 45 wt. % based on the total weight of the composition. In some embodiments, the film-forming agent is present in the composition in an amount of from about 1 to about 45 wt. % based on the total weight of the composition. In some embodiments, the film-forming agent is present in the composition in an amount of from about 15 to about 40 wt. % based on the total weight of the composition. In some embodiments, the film-forming agent is present in the composition in an amount of from about 1 to about 40 wt. % based on the total weight of the composition. In some embodiments, the film-forming agent is present in the composition in an amount of from about 20 to about 35 wt. % based on the total weight of the composition. In some embodiments, the film-forming agent is present in the composition in an amount of from about 1 to about 35 wt. % based on the total weight of the composition. In some embodiments, the film-forming agent is present in the composition in an amount of from about 20 to about 30 wt. % based on the total weight of the composition. In some embodiments, the film-forming agent is present in the composition in an amount of from about 1 to about 25 wt. % based on the total weight of the composition. In some embodiments, the film-forming agent is present in the composition in an amount of from about 1 to about 20 wt. % based on the total weight of the composition. In some embodiments, the film-forming agent is present in the composition in an amount of from about 1 to about 15 wt. % based on the total weight of the composition. In some embodiments, the film-forming agent is present in the composition in an amount of from about 1 to about 10 wt. % based on the total weight of the composition. In some embodiments, the film-forming agent is present in the composition in an amount of from about 1 to about 5 wt. % based on the total weight of the composition.

It is particularly preferred that the composition of the present invention further comprises a fragrance. Preferably the fragrance is selected from essential oils. Preferably the fragrance, and more preferably the essential oil, is present in the solid cosmetic composition in an amount of from 0.001 to 10 wt. % of the solid cosmetic composition. Preferably the fragrance, and more preferably the essential oil, is present in the solid cosmetic composition in an amount of from 0.001 to 8 wt. % of the solid cosmetic composition. Preferably the fragrance, and more preferably the essential oil, is present in the solid cosmetic composition in an amount of from 0.001 to 6 wt. % of the solid cosmetic composition. Preferably the fragrance, and more preferably the essential oil, is present in the solid cosmetic composition in an amount of from 1 to 6 wt. % of the solid cosmetic composition. Preferably the fragrance, and more preferably the essential oil, is present in the solid cosmetic composition in an amount of from 4 to about 6 wt. % of the solid cosmetic composition.

Fruit and herb extracts and juices, vegetable oils and essential oils are all compatible with the composition.

The essential oils may be selected based on the fragrance desired, hair or skin type to be treated and other effects desired based on the well-known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the solid product are selected from Tarragon, Lemon myrtle, Jasmin, Ylang ylang, Labdunum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, *Litsea Cubeba*, Cardamon, Tonka, and Chamomile blue. In one embodiment, the one or more essential oils present in the solid product are selected from Tarragon, Lemon myrtle, Labdunum, and Lemon.

Vitamins, particularly B, C and E are very beneficial for the hair and skin. Vitamin rich ingredients such as Wheatgerm oil can also be used to deliver vitamins on to the hair and skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the solid product of a material, such as a natural material, that has a high vitamin content.

The decorative items which may be present in the solid product include items such as glitter, paper such as rice paper, sequins, dried or fresh flowers, herbs, vegetables, parts thereof or mixtures thereof. Other enhancing materials may also be incorporated In one aspect the solid cosmetic composition comprises at least starch. Preferably the starch is corn starch, tapioca starch or a mixture thereof. Preferably the starch is corn starch or corn flour. The term 'corn starch' used herein refers to the starch of corn (also known as maize) [*Zea mays*] grain and is obtained from the endosperm of the corn kernel. Corn starch is also known in some countries as corn flour or maize starch. Corn starch is not to be confused with cornmeal. Cornmeal is a coarse flour ground from dried maize or corn. In the United Kingdom corn starch is known as corn flour. Corn starch has mainly been used in foods, where it is used as a thickener for sauces and custards. In cosmetics it has been mainly used in talcum powders for babies.

In one aspect the solid cosmetic composition comprises at least soap, surfactant or a mixture thereof. In one aspect the solid cosmetic composition comprises at least soap. The soap present in the compositions described herein may be from any suitable source. In one aspect the soap is saponified vegetable oil or vegetable butter. In one aspect the soap is saponified vegetable oil. In one aspect the solid cosmetic composition comprises at least a surfactant. In one aspect the surfactant is selected from cationic surfactants, non-ionic surfactants, amphoteric surfactants, alkylbenzene sulfonate surfactants, alkyl sulphate surfactants, alkyl ether sulphate surfactants and mixtures thereof. In one aspect the surfactant is selected from sodium lauryl sulphate, sodium cocoamphoacetate, sodium laureth sulphate, lauryl betaine, sodium lauroyl sarcosinate, sodium alkyl sulphate, disodium lauryl sulfosuccinate, disodium laureth sulfosuccinate, cocamide monoethanolamine, cetrimonium bromide, sodium and mixtures thereof. In one aspect the surfactant is selected from sodium lauryl sulphate, lauryl betaine and mixtures thereof. In one aspect the surfactant is sodium lauryl sulphate. In one aspect the surfactant is lauryl betaine. In one aspect the surfactant is a mixture of sodium lauryl sulphate and lauryl betaine.

In one aspect the present invention provides a solid bath melt. As will be understood by one skilled in the art a bath melt is a bath oil or bath butter provided in the form of a solid. The solid bath oil contains emollient butters. When a bath is required by the user, a bar of the solid butter may be placed under the running water of the bath or a part of the bar may be broken off and dropped into the water under the running tap. The solid bath oil melts and dissolves in the warm or hot water and is disbursed in the bath. The solid bath melt may contain a dispersant. In one aspect the dispersant is selected from cationic surfactants, non-ionic surfactants, amphoteric surfactants, alkylbenzene sulfonate surfactants, alkyl sulphate surfactants, alkyl ether sulphate surfactants and mixtures thereof. In one aspect the dispersant is selected from sodium lauryl sulphate, sodium cocoamphoacetate, sodium laureth sulphate, lauryl betaine, sodium lauroyl sarcosinate, sodium alkyl sulphate, disodium lauryl sulfosuccinate, disodium laureth sulfosuccinate, cocamide monoethanolamine, cetrimonium bromide, sodium and mixtures thereof. In one aspect the dispersant is selected from sodium lauryl sulphate, lauryl betaine and mixtures thereof. In one aspect the dispersant is sodium lauryl sulphate. In one aspect the dispersant is lauryl betaine. In one aspect the dispersant is a mixture of sodium lauryl sulphate and lauryl betaine.

The solid cosmetic composition may contain a salt of carbonic acid and acidifying agent. The salt of carbonic acid and the acidifying agent may together provide a carbon dioxide effervescing system. The salt of carbonic acid may be any suitable salt. In one aspect the salt of carbonic acid is selected from alkali metal carbonates, alkali metal bicarbonates and mixtures thereof. In one aspect the salt of carbonic acid is selected from sodium bicarbonate, sodium carbonate and mixtures thereof. In one aspect the salt of carbonic acid is sodium bicarbonate. The acidifying agent may be selected from all suitable acidifying agents. In one aspect the acidifying agent is selected from monocarboxylic acids, dicarboxylic acids, tricarboxylic acids and mixtures thereof. In one aspect the acidifying agent is selected citric acid, potassium bitartrate (cream of tartar) and mixtures thereof. In one aspect the acidifying agent is potassium bitartrate (cream of tartar). In one aspect the acidifying agent is citric acid. In one aspect the salt of carbonic acid is sodium bicarbonate and the acidifying agent is potassium bitartrate (cream of tartar).

The above ranges provide preferred amounts of each of the components. Each of these ranges may be taken alone or combined with one or more other component ranges to provide a preferred aspect of the invention.

Process

As discussed herein, in one aspect there is provided a process for the production of a solid cosmetic composition, wherein the process comprises the steps of:
 (a) providing a solid cosmetic composition comprising;
  (i) one or more vegetable butters in a total amount of 5 to 80 wt. % based on the cosmetic composition;
  (ii) one or more waxes in a total amount of 5 to 45 wt. % based on the cosmetic composition; and
  (iii) one or more emulsifying materials in a total amount of 5 to 40 wt. % based on the cosmetic composition;
 (b) heating the solid cosmetic composition to make the cosmetic composition flowable;
 (c) allowing the flowable cosmetic composition to cool to form the solid cosmetic composition.

In one aspect, the solid cosmetic composition is heated to no greater than 15° C. above its melting point prior to step (c). In one aspect, the solid cosmetic composition is heated to no greater than 10° C. above its melting point prior to step (c). In one aspect, the solid cosmetic composition is heated to no greater than 5° C. above its melting point prior to step (c).

In one aspect, the solid cosmetic composition is heated to no greater than 15° C. above its melting point prior to 3D printing. In one aspect, the solid cosmetic composition is heated to no greater than 10° C. above its melting point prior to 3D printing. In one aspect, the solid cosmetic composition is heated to no greater than 5° C. above its melting point prior to 3D printing.

We have found that the printing process may be improved by 'conditioning' the solid cosmetic composition prior to cooling, for example during printing. In particular, in one aspect the solid cosmetic composition is stored in a dehumidifier prior to printing. In one aspect, the solid cosmetic composition is heated at a temperature of at least 32° C. to make the cosmetic composition flowable. In one aspect, the solid cosmetic composition is heated at a temperature of at least 34° C. to make the cosmetic composition flowable. In one aspect, the solid cosmetic composition is heated at a temperature of from 32 to 40° C. to make the cosmetic composition flowable. In one aspect, the solid cosmetic composition is heated at a temperature of from 32 to 38° C. to make the cosmetic composition flowable. In one aspect, the solid cosmetic composition is heated at a temperature of from 34 to 40° C. to make the cosmetic composition flowable. In one aspect, the solid cosmetic composition is heated at a temperature of from 34 to 38° C. to make the cosmetic composition flowable.

3D Printing

As discussed herein, 3D printing, also known as additive manufacturing (AM), refers to processes used to synthesize a three-dimensional object in which successive layers of material are formed. Objects can be of almost any shape or geometry and are produced using digital model data from a 3D model or another electronic data source. This printing process is extremely flexible and allows for the formation of the products described above. By its nature, the requirement to deliver successive layers of material means that for a process to correctly be defined as 3D printing at least two layers of product must be deposited. The present invention does not encompass processes in which a single layer of product is deposited. In one preferred aspect the solid cosmetic composition comprises at least three layers of cosmetic product which have been deposited by 3D printing, such as at least four layers of cosmetic product, such as at least five layers of cosmetic product, such as at least seven layers of cosmetic product, such as at least ten layers of cosmetic product, such as at least fifteen layers of cosmetic product.

In one aspect the solid cosmetic composition comprises at least one layer of a first cosmetic component and at least one layer of a second cosmetic component, wherein the first cosmetic component and the second cosmetic component are different cosmetic products. In this aspect, a multifunctional cosmetic composition may be delivered. For example, cosmetic formulae or components may be formed into a single product, which have different functional effects for the end user. Furthermore, cosmetic formulae may be delivered in a single product where those cosmetic formulae may have some detrimental interaction during storage. By delivering the cosmetic formulae have individual layers rather than a mixture and overall solid cosmetic composition may be provided which has the function of a mixture of formulae but in which the components are stable during storage.

In one aspect the solid cosmetic composition comprises at least one layer of a first cosmetic component and at least one layer of a second cosmetic component, wherein the first cosmetic component and the second cosmetic component are different colours. The first cosmetic component and the second cosmetic component which are different colours may be the same cosmetic formula or may be different cosmetic formulae. As will be understood, by the same cosmetic formula it is meant a formula which has the same function e.g. a mascara, but which has a different colour. When the first cosmetic component and the second cosmetic component are different formulae, the advantages set out above in respect of layers of different formulae equally apply. Irrespective of whether the formulae are the same or different, this aspect of the invention allows for the provision of solid cosmetic compositions having multiple coloured layers which are attractive to the end user. By forming these multiple layers through 3D printing, it is possible to make a solid cosmetic composition in a more timely manner than a typical moulding process. When multilayer products are made in a mould, it is necessary to form a layer and then wait for it to set before applying and setting a further layer. This can be a time-consuming process and if the first layer has not fully set then "bleed" of colour between the layers can occur. Furthermore, the layers that are delivered can sometimes be imprecise due to the nature of pouring a liquid into a mould. The present invention provides an improved product compared to such a prior system.

The present invention may utilise any 3D printing process. In one aspect the present invention utilises extrusion deposition. The detail/resolution that can be provided for in a product is (in part) determined by the thickness of each layer deposited. This is in turn linked to the size/type of the print head of the 3D printer. In one aspect each layer of the solid cosmetic product which has been deposited by 3D printing has a thickness of no greater than 10 mm. In one aspect at least two layers of the solid cosmetic product which has been deposited by 3D printing has a thickness of no greater than 8 mm, preferably a thickness of no greater than 6 mm. In one aspect each layer of the solid cosmetic product which has been deposited by 3D printing has a thickness of no greater than 8 mm, preferably a thickness of no greater than 6 mm. In one aspect at least two layers of the solid cosmetic product which has been deposited by 3D printing has a thickness of no greater than 5 mm, preferably a thickness of no greater than 2 mm. In one aspect each layer of the solid cosmetic product which has been deposited by 3D printing has a thickness of no greater than 5 mm, preferably a thickness of no greater than 2 mm. In one aspect at least two layers of the solid cosmetic product which has been deposited by 3D printing has a thickness of no greater than 1 mm, preferably a thickness of no greater than 0.5 mm. In one aspect each layer of the solid cosmetic product which has been deposited by 3D printing has a thickness of no greater than 1 mm, preferably a thickness of no greater than 0.5 mm. In one aspect at least two layers of the solid cosmetic product which has been deposited by 3D printing has a thickness of no greater than 0.2 mm, preferably a thickness of no greater than 0.1 mm. In one aspect each layer of the solid cosmetic product which has been deposited by 3D printing has a thickness of no greater than 0.2 mm, preferably a thickness of no greater than 0.1 mm.

As will be understood from the advantages described herein, the present invention allows the preparation of products with complex shapes which would otherwise not be possible to produce. Therefore, in one aspect the solid cosmetic composition has a shape which could not be prepared by forming the solid cosmetic composition in a mould.

The solid cosmetic product may be formed into any suitable size product. The present invention allows for the preparation of small product which could not be readily made through prior systems such as moulding and the preparation of large products which would offer significant difficulties in handling if made with prior systems. Therefore in one aspect the solid cosmetic composition has a mass of from 1 g to 1000 kg, such as a mass of from 1 g to 100 kg.

The shape of the solid products of the present invention is not limited. It may be that the solid products are provided with a shape which would be aesthetically pleasing and/or which aids in the use of the product. For example, it may be that the solid product is in a shape which is ergonomically acceptable to the user.

Method

In one aspect of the present invention, there is provided a method comprising contacting the skin or hair of a user the solid cosmetic composition as defined herein Further aspects of the present invention are described below.

In one aspect there is provided a solid cosmetic composition suitable for 3D printing, wherein the cosmetic composition comprises
(a) one or more vegetable butters in a total amount of 5 to 80 wt. % (such as in a total amount of 20 to 80 wt. %) based on the cosmetic composition;
(b) one or more waxes in a total amount of 5 to 45 wt. % based on the cosmetic composition; and
(c) one or more emulsifying materials in a total amount of 5 to 40 wt. % based on the cosmetic composition.

In one aspect there is provided a solid cosmetic composition prepared by 3D printing, wherein the cosmetic composition comprises
(a) one or more vegetable butters in a total amount of 5 to 80 wt. % based on the cosmetic composition;
(b) one or more waxes in a total amount of 5 to 45 wt. % based on the cosmetic composition; and
(c) one or more emulsifying materials in a total amount of 5 to 40 wt. % based on the cosmetic composition.

In one aspect there is provided a process for the production of a 3D printed solid cosmetic composition, wherein the process comprises the steps of:
(a) providing a solid cosmetic composition comprising;
(i) one or more vegetable butters in a total amount of 5 to 80 wt. % (such as in a total amount of 20 to 80 wt. %) based on the cosmetic composition;
(ii) one or more waxes in a total amount of 5 to 45 wt. % based on the cosmetic composition; and
(iii) one or more emulsifying materials in a total amount of 5 to 40 wt. % based on the cosmetic composition;
(b) heating the solid cosmetic composition to make the cosmetic composition flowable;
(c) 3D printing with the flowable cosmetic composition to form the 3D printed solid cosmetic composition.

In one aspect there is provided a product obtained or obtainable by a process comprises the steps of:
(a) providing a solid cosmetic composition comprising;
(i) one or more vegetable butters in a total amount of 5 to 80 wt. % (such as in a total amount of 20 to 80 wt. %) based on the cosmetic composition;
(ii) one or more waxes in a total amount of 5 to 45 wt. % based on the cosmetic composition; and
(iii) one or more emulsifying materials in a total amount of 5 to 40 wt. % based on the cosmetic composition;
(b) heating the solid cosmetic composition to make the cosmetic composition flowable;
(c) 3D printing with the flowable cosmetic composition to form the 3D printed solid cosmetic composition.

In one aspect there is provided a cosmetic method comprising contacting the skin or hair of a user with a solid cosmetic composition prepared by 3D printing, wherein the cosmetic composition comprises
(a) one or more vegetable butters in a total amount of 5 to 80 wt. % (such as in a total amount of 20 to 80 wt. %) based on the cosmetic composition;
(b) one or more waxes in a total amount of 5 to 45 wt. % based on the cosmetic composition; and
(c) one or more emulsifying materials in a total amount of 5 to 40 wt. % based on the cosmetic composition.

EXAMPLES

Example 1

The invention will now be described with reference to the following non-limiting examples.

| Phase | Material type | Component | Description | Amount (wt. %) |
|---|---|---|---|---|
| A | Waxes | Carnauba wax | Give product solidity | 12.0 |
| | | Japan wax | | 2.9 |
| | Emulsifying materials | Stearic acid | Give solidity | 5.0 |
| | | Mixture of glycerol monostearate and PEG-100 stearate (in 1:1 wt ratio) | | 12.0 |
| | Butters | Illipe butter | Melting temperature profile allows for 3 D printing whilst giving a solid product which releases pigment. | 21.5 |
| | | Cupuacu butter | | 2.0 |
| | | Cocoa butter | Conditions the lashes. | 11.5 |
| B | Vegetable oil | Castor oil | A 'heavy' oil which 'collects' and acts as an effective carrier for the pigment | 9.0 |
| C | Polymers | PVP | Provides hold and definition on the lashes | 8.0 |
| D | Pigments | Black iron oxide | Colours the lashes (or other hair) | 11.3 |
| | | Talc | Inert carrier - improves the deposition of the black pigment. Not always required depending on pigment. | 4.8 |

PVP = polyvinylpyrrolidone
PEG-100 stearate = ester of polyethylene glycol and stearic acid wherein the polyethylene glycol has 100 ethylene glycol units.

The above composition was formed into a base product in accordance with the following method:
1. Melt A to 75° C. Ensure the waxes are melted.
2. Stir C into B and warm to 75° C.
3. With A and B/C both at 75° C., emulsify B/C into A.
4. Grind D together.
5. Add D gradually to A/B/C.
6. (optional) pour into moulds and leave to set.

The based product was then 3D printed as follows:
1. Preheat the product syringe to −32° C. in a dehumidifier oven.
2. If a set product is being used, grate it into the preheated syringe. If the product is already molten, pour into the preheated syringe.
3. Attach the syringe to the nozzle and set the syringe temperature controller to −36° C.
4. Print according to the following 3D printer settings Print Speed: 150%, Layer Height: 1.5; Printing Width: 1.5; Nozzle Size: 1.5; Infill Density: 100%; Extrusion Rate: 0.8

The machine used was a Focus 3D Food printer by byFlow. A nozzle made of machined aluminium has been fitted, around which is a heating controller—this allows the syringe and deposition nozzle temperature to be precisely controlled. It helped achieved a constant deposition and to avoiding hardening/clogging inside the nozzle. It was also found that initially the first few layers of the product were not adhering to the substrate correctly. To counteract this, a pre-cooled granite substrate is used to quickly cool and set the product on initial contact, thus achieving a tidier final product.

Figure 1B:
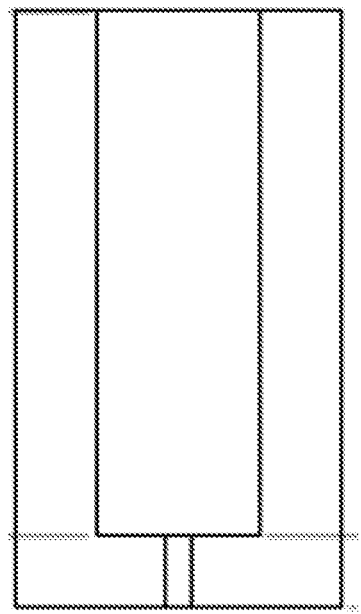
FIG. 1b is a vertical section of a 3D model of a solid mascara prepared in accordance with the present invention.
Figure 1C:
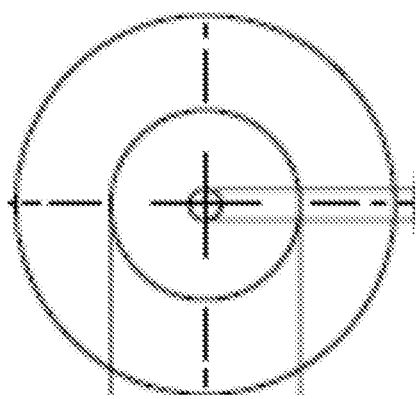
FIG. 1c is a horizontal section of a 3D model of a solid mascara prepared in accordance with the present invention.

A print for an 8 g product having the shape of FIGS. 1a to 1c took approximately 4 minutes.

The mascara product was used by inserting a standard mascara brush into the hole of the cylinder after the brush was wetted with water. The mascara product was readily picked up by the brush and was then applied to the eye lashes of the user. The product was easily applied to the lashes without clumping of the product and provided the required cosmetic effect on the lashes. The product was worn by the user for an extended period and no running of the mascara product was observed.

Example 2 (Comparative)

The following comparative formulation was prepared using the method below.

| Phase | Component | Amount (wt. %) |
| --- | --- | --- |
| A | Cocoa butter | 36.65 |
|  | Japan wax | 5.5 |
|  | Stearic acid | 4.8 |
|  | Illipe butter | 10.6 |
|  | Cupuacu butter | 3.9 |
| B | Castor oil | 8.5 |
|  | PVP/VA | 12.0 |
| C | Black iron oxide | 11.3 |
|  | Talc | 4.8 |

PVP/VA = polyvinylpyrrolidone/vinyl acetate

1. Melt A to 75° C. Ensure the waxes are melted.
2. Make a solution of B. Warm to 75° C.
3. Stir B into A and emulsify gently
4. Grind C together.
5. Add C gradually to A/B and pour into container The comparative formulation was then 3D printed using the method of Example 1.

The mascara product was used by inserting a standard mascara brush into the hole of the cylinder after having dipped the brush in water. The mascara product was picked up by the brush and was then applied to the eye lashes of the user. The product was found to readily smudge on the skin surrounding the lashes and had to be removed by the user.

Example 3

| Phase | Component | Amount (wt. %) |
| --- | --- | --- |
| A | Cocoa butter | 10.00 |
|  | Illipe Butter | 10.00 |
|  | Cupuacu butter | 5.00 |
|  | Japan wax | 2.90 |
|  | Stearic acid | 5.00 |
|  | Glyceryl stearate (and) PEG-100 stearate | 15.00 |
|  | Phenoxyethanol | 0.50 |
| B | Castor oil | 5.00 |
|  | Gum Acacia | 3.00 |
|  | PVP/VA | 5.00 |
|  | SYNTRAN ® 5760 | 21.80 |
| C | Black Iron Oxide | 12.00 |
|  | Talc | 4.80 |

Example 3 was prepared in the same manner as Example 2.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A solid cosmetic composition, wherein the cosmetic composition comprises:
    one or more vegetable butters in a total amount of 20 to 55 wt. % based on the cosmetic composition, wherein the one or more vegetable butters are selected from Cocoa butter, Illipe butter, Murumuru butter, Kokum butter, Aloe butter, Avocado butter, Cupuacu butter, Macadamia Nut butter, Mango butter, Olive butter, Shea butter, Coconut butter, Pumpkin Seed butter, Peanut butter, Almond butter, Coffee Bean butter, Refined butter, Hemp Seed butter, Mochacchino butter, Pistachio Nut butter, Shealoe butter, and mixtures thereof;
    one or more waxes in a total amount of 3 to 30 wt. % based on the cosmetic composition, wherein the one or more waxes are selected from carnauba wax, candelilla, Japan wax, beeswax, rapeseed wax, sunflower wax, orange peel wax, rose wax, paraffin wax, ozocerite wax and mixtures thereof;
    one or more emulsifying materials in a total amount of 5 to 40 wt. % based on the cosmetic composition; and
    a film-forming agent selected from natural polymers, wherein the film-forming agent is present in the composition in an amount of from about 1 to about 20 wt. % based on the total weight of the composition.

2. The solid cosmetic composition according to claim 1, wherein the one or more emulsifying materials are in a total amount of 10 to 25 wt. % based on the cosmetic composition.

3. The solid cosmetic composition according to claim 1, wherein the one or more vegetable butters are selected from Cocoa butter, Illipe butter, Cupuacu butter and mixtures thereof.

4. The solid cosmetic composition according to claim 1, wherein the one or more emulsifying materials are selected from stearic acid and salts thereof, glycerol monostearate, esters of polyethylene glycol and stearic acid, cetearyl olivate, sorbitan olivate, triethanolamine and mixtures thereof.

5. The solid cosmetic composition according to claim 1, wherein the cosmetic composition further comprises one or more vegetables oils in a total amount of 2 to 15 wt. % based on the cosmetic composition.

6. The solid cosmetic composition according to claim 5 wherein the one or more vegetable oils are selected from almond oil, jojoba oil, castor oil, olive oil, grape seed oil, argan oil, moringa oil, baobab oil, rose hip oil, kalahari melon oil, brazil nut oil, sacha inchi nut oil, corn oil, soya bean oil, sunflower oil, avocado oil, macadamia oil, pumpkin seed oil, evening primrose oil, apricot kernel oil, flaxseed oil, poppy seed oil, broccoli seed oil, rice bran oil, wheatgerm oil, and mixtures.

7. The solid cosmetic composition according to claim 5, wherein the vegetable oil is at least castor oil.

8. The solid cosmetic composition according to claim 1, wherein the solid cosmetic composition further comprises at least one or more cosmetic components selected from colours, pigments, binders, fillers, emulsifiers, opacifiers, perfumes, fragrances, decorative items, humectants, honey, sugars, sugar alcohols, soaps, surfactants, fruits, vegetables, clays, herbs, cereals, beans, proteins, scrubs, exfoliants, starches, preservatives, quaternary ammonium compounds, carbon dioxide effervescent components, and mixtures thereof.

9. The solid cosmetic composition according to claim 1, wherein the solid cosmetic composition is selected from make-up fragrances, bath products, massage bars, cleansing products, hair products and combinations thereof.

10. The solid cosmetic composition according to claim 1, wherein the solid cosmetic composition is mascara.

11. The solid cosmetic composition according to claim 1, wherein the film-forming agent is gum acacia.

12. The solid cosmetic composition according to claim 1, wherein the solid cosmetic composition is free of external packaging.

13. The solid cosmetic composition according to claim 1, wherein the solid cosmetic composition is mascara, wherein the mascara is configured for use with an eyelash brush and applied to lashes of a user without running.

14. The solid cosmetic composition according to claim 1, wherein the solid cosmetic composition is mascara, wherein the mascara is configured for use with an eyelash brush.

15. The solid cosmetic composition according to claim 1, wherein the solid cosmetic composition is mascara, wherein the mascara is configured to transfer pigment to a wetted eyelash brush.

* * * * *